US009854822B2

(12) United States Patent
Kringelum et al.

(10) Patent No.: US 9,854,822 B2
(45) Date of Patent: Jan. 2, 2018

(54) PROCESS FOR INCREASING THE YIELD OF *LACTOCOCCUS LACTIS* SUBSP, *LACTIS* AND/OR *LACTOCOCCUS LACTIS* SUBSP. *CREMORIS* BACTERIA CULTURES DURING AEROBIC FERMENTATION

(75) Inventors: Børge Windel Kringelum, Ballerup (DK); Niels Martin Sørensen, Copenhagen SV (DK); Christel Garrigues, Frederiksberg C (DK); Martin B. Pedersen, Copenhagen S (DK); Susanne Grøn, Hellerup (DK)

(73) Assignee: CHR. HANSEN A/S, Hoersholm (DK)

( * ) Notice: Subject to any disclaimer, the term of this patent is extended or adjusted under 35 U.S.C. 154(b) by 1899 days.

(21) Appl. No.: 11/813,338

(22) PCT Filed: Jan. 5, 2006

(86) PCT No.: PCT/DK2006/050001
§ 371 (c)(1),
(2), (4) Date: Mar. 17, 2008

(87) PCT Pub. No.: WO2006/072257
PCT Pub. Date: Jul. 13, 2006

(65) Prior Publication Data
US 2008/0171028 A1 Jul. 17, 2008

Related U.S. Application Data

(60) Provisional application No. 60/641,133, filed on Jan. 5, 2005.

(30) Foreign Application Priority Data

Jan. 5, 2005 (DK) .................................. 2005 00020
Sep. 9, 2005 (DK) .................................. 2005 01259

(51) Int. Cl.
C12N 1/20 (2006.01)
A23K 10/18 (2016.01)
A23C 9/123 (2006.01)
A23C 15/12 (2006.01)
A23C 19/032 (2006.01)
C12N 1/38 (2006.01)
A23L 27/24 (2016.01)
A23L 33/135 (2016.01)
A23L 13/70 (2016.01)

(52) U.S. Cl.
CPC .............. *A23K 10/18* (2016.05); *A23C 9/123* (2013.01); *A23C 15/123* (2013.01); *A23C 19/0323* (2013.01); *A23L 13/74* (2016.08); *A23L 27/24* (2016.08); *A23L 33/135* (2016.08); *C12N 1/20* (2013.01); *C12N 1/38* (2013.01)

(58) Field of Classification Search
None
See application file for complete search history.

(56) References Cited

U.S. PATENT DOCUMENTS

| 3,359,177 A | 12/1967 | Nara et al. | |
| 6,787,348 B1* | 9/2004 | Kringelum et al. | ........ 435/252.9 |
| 2005/0032196 A1* | 2/2005 | Duwat et al. | .............. 435/252.9 |

FOREIGN PATENT DOCUMENTS

| EP | 1 038 951 A1 | 9/2000 |
| EP | 1 048 215 B1 | 8/2004 |
| EP | 1 447 442 A1 | 8/2004 |
| EP | 1 493 806 A1 | 1/2005 |
| GB | 746834 | 3/1953 |
| GB | 2 127 845 A | 9/1983 |
| WO | WO 00/05342 | 2/2000 |
| WO | WO 00/39281 | 7/2000 |
| WO | WO 01/52668 A2 | 7/2001 |
| WO | WO 2005/003327 A1 | 1/2005 |

OTHER PUBLICATIONS

Martinussen et al., Journal of Bacteriology, 1994, vol. 176. No. 5, p. 1514-1516.*
Sievers, G., Biochimica et Biophysica Acta, 579 (1979) 181-190.*
Dahiya et al., J. Dairy Sci. 1964, 47(4), pp. 374-377.*
Gaudu et al., Antonie van Leeuwenhoek 82: 263-269, 2002.*
Li et al,. Applied and Environmental Microbiology, Oct. 2003, p. 5739-5745 vol. 69, No. 10.*
Carcoba et al., Eur Food Res Technol (2000) 211 :433-437.*
Esmond E. Snell et al., "Proceedings of the National Academy of Sciences", vol. 27, No. 1, Jan. 15, 1941, pp. 1-7.
Stephen J. Fey et al., "Proteome analysis of *Saccharomyces cerevisiae*: A methodological outline", Electrophoresis 1997, 18, 1361-1372.
Christophe Gitton et al., "Proteomlc Signature of *Lactococcus lactis* NCD0763 Cultivated in Milk", Applied and Environmental Microbiology, vol. 71, No. 11, Nov. 2005, pp. 7152-7163.
Peter Ruhdal Jensen et al., "Minimal Requirements for Exponential Growth of *Lactococcus lactis* ", Applied and Environmental Microbiology, vol. 59, No. 12, Dec. 1993, pp. 4363-4366.
Dan Nilsson et al., "Cloning and Expression of the *Lactococcus lactis parDEK* Genes, Required for Growth in Milk", Applied and Environmental Microbiology, vol. 64, No. 11, Nov. 1998, p. 4321-4327.
Karin Vido et al., "Proteome Analyses of Heme-Dependent Respiration in *Lactococcus lactis*: Involvement of the Proteolytic System" Journal of Bacteriology, Mar. 2004, vol. 186, No. 6, pp. 1648-1657.
Magensen et al., "Inventory of Microorganisms with a Documented History of Use in Food", Bulletin of the IDF 377, pp. 10-19, 2002.
Mogens Kilstrup et al., "Nucleotide metabolism and its control in lactic acid bacteria", FEMS Microbiology Reviews 29 (2005) pp. 555-590.
Agnar P. Nyggard et al., "Nutrition Studies of Two Variants of Lactobacillus gayoni", Journal of Bacteriology, vol. 61, No. 4, Apr. 1951, pp. 497-505.

(Continued)

Primary Examiner — Irene Marx
(74) Attorney, Agent, or Firm — Foley & Lardner LLP

(57) ABSTRACT

Microbial starter cultures. More specifically, a method for preparing a microbial starter culture wherein the microorganism is inoculated in a culture medium comprising at least one 5 yield enhancing agent selected from the group consisting of a purine base, a pyrimidine base, a nucleoside and a nucleotide. Such microbial starter cultures are useful in the manufacturing of food, feed and pharmaceutical products.

12 Claims, 3 Drawing Sheets

(56) References Cited

OTHER PUBLICATIONS

Donald E. Weinman et al., "Unidentified Growth Factor for a Lactic Acid Bacterium", Journal of Bacteriology, vol. 87, No. 2, Feb. 1964, pp. 269-269.
George Maxwell Richardson, "CCCV. The Nutrition of *Staphylococcus aureus*. Necessity for Uracil in Anaerobic Growth", Biochem J. 30, pp. 2184-2190, (1936).
J.L. Stokes, "Substitution of thymine for "Folic Acid" in the Nutrition of Lactic Acid Bacteria", Journal of Bacteriology vol. 48, No. 2, Aug. 1944, pp. 201-209.
Martin B. Pedersen et al., "Aerobic Respiration Metabolism in Lactic Acid Bacteria and Uses in Biotechnology", Annu. Rev. Food Sci. Technol. 2012, 3:37-58.
Rob Brooijimans et al., "Heme and menaquinone induced electron transport in lactic acid bacteria", Microbial Cell Factories 2009, 8:28.

\* cited by examiner

PROCESS FOR INCREASING THE YIELD OF *LACTOCOCCUS LACTIS* SUBSP, *LACTIS* AND/OR *LACTOCOCCUS LACTIS* SUBSP. *CREMORIS* BACTERIA CULTURES DURING AEROBIC FERMENTATION

FIELD OF THE INVENTION

The present invention relates to the field of microbial starter cultures. More specifically, the invention provides a method for preparing a lactic acid bacteria (LAB) starter culture wherein the lactic acid bacteria is inoculated in a culture medium comprising at least one yield enhancing agent selected from the group consisting of one or more compound(s) involved in the biosynthesis of nucleic acids or one or more derivative(s) of any such compounds. Such starter cultures are useful in the manufacturing of food, feed and pharmaceutical products.

TECHNICAL BACKGROUND OF THE INVENTION

Microbial cultures are used extensively in the food, feed and pharmaceutical industry in the manufacturing of fermented products including most dairy products such as cheese, yoghurt and butter, but also in meat, bakery, wine or vegetable products. Furthermore, microbial cultures are also used to produce proteins including enzymes and various kinds of useful compounds. Such microbial cultures are usually referred to as starter cultures and are produced at industrial propagation plants and distributed to the fermentation industry, such as to a dairy plant, where the starter culture is used in their production processes. In particularly cultures of lactic acid bacteria are widely used as starter cultures.

As used herein the term "lactic acid bacterium" (LAB) designates a gram-positive, microaerophilic or anaerobic bacterium which ferments sugars with the production of acids including lactic acid (as the predominantly produced acid), acetic acid and propionic acid. The industrially most useful lactic acid bacteria are found among *Lactococcus* species (spp.), *Streptococcus* spp., *Lactobacillus* spp., *Leuconostoc* spp., *Pediococcus* spp., *Brevibacterium* spp, *Enterococcus* spp. and *Propionibacterium* spp. Additionally, lactic acid producing bacteria belonging to the group of the strict anaerobic bacteria, bifidobacteria, i.e. *Bifidobacterium* spp. which are frequently used as food starter cultures alone or in combination with lactic acid bacteria, are generally included in the group of lactic acid bacteria. Even certain bacteria of the species *Staphylococcus* (e.g.: *S. carnosus, S. equorum, S. sciuri, S. vitulinus* and *S. xylosus*) have been referred to as LAB (Mogensen et al. (2002) Bulletin of the IDF No. 377, 10-19).

The production of LAB starter cultures involves the inoculation of LAB cells in a specific fermentation medium with an appropriate number of the cells to be propagated under appropriate fermentation conditions. In the industrial setting much effort is put into obtaining that the concentration of the propagated cells is high towards the end of the fermentation process. This makes heavy demands on the fermentation conditions and the fermentation medium, which has to support growth of the cells in order to obtain the desired high biomass yields.

The optical density of liquid medium at 600 nm ($OD_{600}$) is an accurate means of evaluating the density of bacterial cells in a sample of culture. By the term a "high Optical Density-conditions" is referred to fermentations which is characterized by that the concentration of the propagated cells sufficiently high to result in an $OD_{600}$, which is 10, or more at the end of the fermentation process.

To keep production costs low, industrial fermentations are normally carried out using complex undefined fermentation media. Major components of such media can be yeast extract, cornstarch, whey protein or other milk-based media, which all have complex compositions. For selected fermentation chemically defined media are used which often are made from pure chemicals. Pure chemicals, such as a specific energy or carbon sources, are also often added to complex fermentation media for specific purposes. In either case, the composition of the fermentation medium may be optimal for the viability of the microbial cells, but not optimal for obtaining a high biomass yield of the microorganism.

Most compounds, which are required for cell growth, cost energy for the cell to produce. It often requires that genes encoding the respective biosynthetic enzymes be expressed. The synthesis of these enzymes requires both amino acids and energy. This puts a "protein burden" on the cell, as it must synthesize relatively more enzymes to be able to grow. The precursors required to form the cellular components must furthermore be taken from other pathways, again leading to an additional burden for the cell.

Certain compounds involved in the biosynthesis of nucleic acids have been found to act as so-called cryoprotective agents and reduces the damaging effects on the viability of living cells during freezing and thawing procedures. WO 00/39281 describes the use of inosinate (IMP) and other compounds involved in the biosynthesis of DNA to stabilize the metabolic activity of a liquid starter culture during storage.

It is well-known that LAB have complex growth-factor requirements and that compounds involved in the biosynthesis of DNA and/or RNA stimulate the growth of LAB in chemically defined media. However, several reports show that even though the addition of such compounds result in a shorter lag phase or a higher initial growth rate the addition result in no or only slightly increased yields (Klistrup (2005) FEMS Microbiol Rev. 29, 555-590; Nygaard (1951) J Bact 61, 497-505; Weinman (1964) J Bact 87, 263-269). The addition of compounds involved in the biosynthesis of DNA may even inhibit the yield (Weinman (1964) J Bact 87, 263-269).

As illustrated in examples 3 and 4 the addition of addition of compounds involved in the biosynthesis of DNA also did not increase the biomass yield of fermentations performed high Optical Density-conditions.

Accordingly, there is a need to provide novel approaches to increasing microbial cell biomass yield during fermentation at high Optical Density-conditions.

SUMMARY OF THE INVENTION

The problem to be solved by the present invention is to provide a method for preparing a microbial culture of LAB to obtain increased yields at high Optical Density-conditions.

In 1936 Richardson (Biochem J. 30, 2186) reported that uracil was essential for the anaerobic growth of *Staphylococcus*, but not for aerobic growth of the same organism. Thus it was a complete surprise to find that it was possible to enhance the biomass yield during the aerobic cultivation or production of a LAB starter culture by adding a compound involved in the biosynthesis of nucleic acids to a complex fermentation medium.

Accordingly, a first aspect of the invention relates to a method for obtaining increased yields of a lactic acid bacteria culture fermented under aeration and high Optical Density-conditions, said method comprising the steps of
  i) culturing a lactic acid bacteria in a culture medium and at conditions that allows the fermentation to proceed beyond an Optical Density measured at 600 nm ($OD_{600}$) of 10, wherein said culture medium comprise at least one yield enhancing agent selected from the group consisting of a purine base, a pyrimidine base, a nucleoside, a nucleotide and derivatives thereof at a concentration that ensure that the culture medium comprise at least 1 µM of said at least one yield enhancing agent at the termination of the fermentation; and
  ii) harvesting said lactic acid bacteria to obtain the lactic acid bacteria culture,
wherein the yield enhancing agent results in an increased yield of harvested lactic acid bacteria as compared to culturing the microorganism at identical conditions and in an similar medium which comprise less than 1 µM of each yield enhancing agent at end of the fermentation.

Preferably said culture medium comprises at least 5 µM of at least one yield enhancing agent, such as at least 10 µM, e.g. at least 50 µM of at least one yield enhancing agent. In particularly said culture medium comprise at least 5 µM of the agent(s) which is/are selected from the group of IMP, GMP, inosine and guanine.

Preferably said similar medium comprises less than 5 µM of each yield enhancing agent, such as less than 1 µM, e.g. less than 0.5 µM of each yield enhancing agent. In particularly said similar medium which comprise less that 5 µM of the agent(s) which is/are selected from the group of IMP, GMP, inosine and guanine.

A second aspect of the invention relates to a starter culture obtainable by the method according to the first aspect and embodiments thereof as describe herein.

A third aspect of the invention relates to a culture medium comprising at least one yield enhancing agent selected from the group consisting of a purine base, a pyrimidine base, a nucleoside, a nucleotide and derivatives thereof.

A fourth aspect of the invention relates to a method of preparing a food product, feed product, a pharmaceutical product, a dairy flavor and a cheese flavoring product, said method comprising adding an effective amount of the microbial starter culture according to the second aspect of the invention and embodiments thereof as described herein to a food, feed or pharmaceutical product starting material and keeping the thus inoculated starting material under conditions where the microorganism is metabolically active.

A fifth aspect of the invention relates to a fermented food, feed or pharmaceutical product obtainable by the method of the fourth aspect and embodiments thereof as described herein.

DEFINITIONS

Prior to a discussion of the detailed embodiments of the invention is provided a further definition of specific terms used herein.

Herein, the term "purine base" is intended to cover a cyclic nitrogen-containing base having the core structure of purine. Thus, in the present context, the term "purine base" is intended to mean an optionally substituted purine. Specific examples of purine bases include adenine, guanine, xanthine and hypoxanthine.

Analogously, the term "pyrimidine base" is intended to cover a cyclic nitrogen-containing base having the core structure of pyrimidine. Thus, in the present context, the term "pyrimidine base" is intended to mean an optionally substituted pyrimidine. Specific examples of pyrimidine bases include cytosine, thymine and uracil.

In the present context the term "nucleotide" means a 2-deoxyribose (DNA) monomer or a ribose (RNA) monomer which is bonded through its number one carbon atom to a purine base, such as adenine, guanine, xanthine or hypoxanthine, or which is bonded through its number one carbon atom to a pyrimidine base, such as cytosine, thymine or uracil. Further, the DNA or RNA monomer is bonded through its number five-carbon atom to a phosphate group. Specific examples of nucleotides include adenosine monophosphate (AMP), guanosine monophosphate (GMP), uridine monophosphate (UMP), cytidin monophosphate (CMP), xanthine monophosphate (XMP), inosine monophosphate (IMP), deoxyadenosine monophosphate (dAMP), deoxyguanosine monophosphate (dGMP), thymidine monophosphate (dTMP), deoxycytidin monophosphate (dCMP), deoxyxanththin monophosphate (dXMP) and deoxyinosine monophosphate (dIMP). IMP is particularly preferred.

When used herein, the term "nucleoside" is intended to mean a 2-deoxyribose (DNA) monomer or a ribose (RNA) monomer which is bonded through its number one carbon atom to a purine base, such as adenine, guanine, xanthine or hypoxanthine, or which is bonded through its number one carbon atom to a pyrimidine base, such as cytosine, thymine or uracil. Specific examples of nucleosides include adenosine, guanosine, uridine, cytidine, inosine, deoxyadenosine, deoxyguanosine, deoxythymidine, deoxycytidine and deoxyinosine. Inosine is particularly preferred.

As will be understood from the above definitions of the terms "nucleoside" and "nucleotide", a nucleotide may be considered a nucleoside comprising a phosphate group bonded through the number five-carbon atom of the sugar unit. Accordingly, the nucleotides described herein may also be referred to as "nucleoside"-5'-monophosphate. For example, inosinate (IMP) may be referred to as inosine-5'-monophosphate, deoxyinosinate (dIMP) may be referred to as deoxyinosine-5'-monophosphate, etc.

In the present context, the term "derivative", when used in connection with the terms "nucleotide" or "nucleoside" is intended to mean that the nucleotide or the nucleoside in question has been modified in its sugar (i.e. 2-deoxyribose or ribose) unit, or that the nucleotide or the nucleoside in question has been modified in its cyclic nitrogen-containing base, or that the nucleotide or nucleoside in question has been modified in both its sugar unit and in its cyclic nitrogen-containing base. For example, the 2'-H group of the deoxyribose unit or the 2'-OH group of the ribose unit may have been modified, e.g. by incorporation of a 2'-F group, a 2'-O-methyl group, and the like. Likewise, the cyclic nitrogen-containing base may contain one or more substitutents not normally found in adenine, guanine, xanthine, hypoxanthine, cytosine, thymine and uracil. Specific examples include 5-methylcytosine ($^{Me}C$), isocytosine, pseudoisocytosine, 5-bromouracil, 5-propynyluracil, 5-propyny-6-fluorouracil, 5-methylthiazoleuracil, 6-aminopurine, 2-aminopurine, 2,6-diaminopurine, 7-propyne-7-deazaadenine, 7-propyne-7-deazaguanine and 2-chloro-6-aminopurine.

As used herein, the term "fermentation" refers to a process of propagating or cultivating a microbial cell under aerobic or anaerobic conditions.

The term "starter culture" refers to a preparation containing microbial cells that is intended for inoculating a medium to be fermented.

In the present context, the term "yield" refers to the amount of biomass produced in a fermentation of a given volume. The yield may be measured in many ways; here the yield is measured in two different ways. 1) As biomass per unit of volume measured (background subtracted) by the Optical Density at 600 nm ($OD_{600}$) of a 1 cm light path of the fermentation medium at the end of the fermentation or 2) by kg of F-DVS culture with an "acidification activity" of 4.8-5.1 according to the according to Pearce test described in Example 2: Analytical Procedure QAm-043 at end of the fermentation.

The term "F-DVS" refers to a so-called frozen Direct Vat Set cultures as described in Example 1.

The term "Porphyrin compound" refers to cyclic tetrapyrrole derivatives whose structures are derived from that of porphyrin by substitution of the carbons located at the apices of the pyrrole core, by various functional groups. It also refers to complexes of the said derivatives with a metal atom that forms coordinate bonds with two of the four nitro gens of the porphyrin ring. This definition encompasses, but is not limited to: uroporphyrins, coproporphyrins, protoporphyrins and haematoporphyrins, as well as their salts and esters and their complexes with a metal atoms. Particularly preferred porphyrin compounds are protoporphyrin IX and its complexes with an iron atom, in particular haem and hemin, and the derivatives of chlorophyll, such as chlorophyllins.

In the present context, the expression "lactic acid bacteria" (LAB) designates a group of Gram positive, catalase negative, non-motile, microaerophilic or anaerobic bacteria that ferment sugar with the production of acids including lactic acid as the predominantly produced acid, acetic acid, formic acid and propionic acid. The industrially most useful lactic acid bacteria are found among *Lactococcus* species (spp.), *Streptococcus* spp., *Lactobacillus* spp., *Leuconostoc* spp., *Pediococcus* spp., *Brevibacterium* spp, *Enterococcus* spp. and *Propionibacterium* spp. Additionally, lactic acid producing bacteria belonging to the group of the strict anaerobic bacteria, bifidobacteria, i.e. *Bifidobacterium* spp. which are frequently used as food starter cultures alone or in combination with lactic acid bacteria, are generally included in the group of lactic acid bacteria. Even certain bacteria of the species *Staphylococcus* (e.g.: *S. carnosus*, *S. equorum*, *S. sciuri*, *S. vitulinus* and *S. xylosus*) have been referred to as LAB (Mogensen et al. (2002) Bulletin of the IDF No. 377, 10-19).

Commonly used LAB starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include *Lactococcus lactis*, *Lactococcus lactis* subsp. *cremoris*, *Leuconostoc mesenteroides* subsp. *cremoris*, *Pediococcus pentosaceus*, *Lactococcus lactis* subsp. *lactis biovar. diacetylactis*, *Lactobacillus casei* subsp. *casei* and *Lactobacillus paracasei* subsp. *paracasei*. Thermophilic lactic acid bacterial species include as examples *Streptococcus thermophilus*, *Enterococcus faecium*, *Lactobacillus delbrueckii* subsp. *lactis*, *Lactobacillus helveticus*, *Lactobacillus delbrueckii* subsp. *bulgaricus* and *Lactobacillus acidophilus*.

Due to the fact that the amount and hence the concentration of the yield enhancing agent in the medium may change over time, e.g. due to incorporation into the microbial cells, it is necessary to refer to a specific point in time where the concentration of yield enhancing agent has to be measured or determined. Therefore, the term "initially", when used in connection with the concentration of yield enhancing agent in the medium, refers to the concentration of yield enhancing agent present in the medium immediately before the microbial cells to be cultured are added to the medium or, alternatively, to the concentration of yield enhancing agent present in the medium immediately after the microbial cells to be cultured have been added to the medium.

A significant application of the starter culture according to the invention is as so-called probiotics. In the present context, the term "probiotic" is to be understood as microbial cultures which, when ingested in the form of viable cells by humans or animals, confer an improved health condition, e.g. by suppressing harmful microorganisms in the gastrointestinal tract, by enhancing the immune system or by contributing to the digestion of nutrients. A typical example of such a probiotically active product is "sweet acidophilus milk".

Embodiments of the present invention are described below, by way of examples only.

DETAILED DISCLOSURE OF THE INVENTION

According to invention the solution to the problem of providing a method for preparing a microbial culture of LAB to obtain increased yields at high Optical Density-conditions is to ferment the culture under aerobic conditions and in a medium which comprise at least one yield enhancing agent selected from the group consisting one or more compound(s) involved in the biosynthesis of nucleic acids or one or more derivative(s) of any such compounds.

Without being limited to a particular theory, it is contemplated that the increased yield relates to a situation wherein at least one yield enhancing agent continues to appear in the fermentation medium throughout the complete fermentation. It is observed that the exhausting of yield enhancing agents from the medium result in the onset of de novo synthesis of various enzyme systems (see example 6), and it is assumed that such energy-demanding de novo synthesis results in a reduced yield.

The situation wherein at least one yield enhancing agent continues to appear in the fermentation medium throughout the complete fermentation may be obtained by culturing the LAB in a medium which initially comprise sufficient yield enhancing agent to ensure that at least one such agent remain in the medium throughout the complete fermentation. One such medium is a culture medium initially comprise at least 1 mM, preferably at least 3 mM and even more preferred at least 3 mM of at least one yield enhancing agent selected from the group consisting one or more compound(s) involved in the biosynthesis of nucleic acids or one or more derivative(s) of any such compounds.

Such medium may be obtained by formulating the media using components which are particularly rich with respect to yield enhancing agents selected from the group consisting one or more compound(s) involved in the biosynthesis of nucleic acids or one or more derivative(s) of any such compounds. One such component could be yeast extract, in particularly so-called "enriched" or "fortified" yeast extract preparations, which are particularly rich in purines and/or pyrimidines.

Instead of formulating the medium using preparations, which are particularly rich in yield enhancing agents, purified agents may be added to otherwise standard media formulations. For instance the culture medium may be a complex fermentation medium to which at least 0.2 g, preferably at least 0.8 g and even more preferred at least 2 g of at least one yield enhancing agent has been added per L.

It is also possible to ensure that at least one yield enhancing agent remain in the medium throughout the complete fermentation by one or more additions of said at least one yield enhancing agent is added the fermentation.

The present invention is particular useful at the high Optical Density-conditions which is strived for in many industrial settings. In a selected embodiment of the present invention said high Optical Density-conditions are characterized by an $OD_{600}$ above 15, preferably above 20, more preferably above 30, even more preferably over 40 and most preferably over 50 at the termination of the fermentation.

In a preferred embodiment, wherein said increased yield of harvested microorganism of the method of the first aspect is increased by a factor of at least 1.2, preferably by a factor of at least 1.3, more preferably by a factor of at least 1.4, even more preferably by a factor of at least 1.5 and most preferably by a factor of at least 1.6.

According to the invention the microorganism is fermented at aerobic conditions. Preferably the fermentation of the microbial culture is performed under aeration and in a nutrient medium, in which at least one porphyrin compound is present or is added. In a preferred embodiment the LAB is cultured under aeration in a prophyrin-containing nutrient medium as described in WO00/0542 wherein said medium further comprise at least one yield enhancing agent selected from the group consisting one or more compound(s) involved in the biosynthesis of nucleic acids or one or more derivative(s) of any such compounds. WO00/0542 is hereby enclosed by reference. Aeration can be effected by any means known by one skilled in the Art, for example by shaking or stirring the culture medium, or by passing a gaseous mixture containing oxygen such as air, into the culture medium.

In a preferred embodiment said yield enhancing agent is selected from the group consisting of a purine base, a pyrimidine base, a nucleoside, a nucleotide and derivatives thereof.

Said yield enhancing agent may be a purine base preferably a purine base is selected from the group consisting of adenine, guanine, xanthine and hypoxanthine.

Said yield enhancing agent may be a pyrimidine base, preferably a pyrimidine base is selected from the group consisting of cytosine, thymine and uracil.

Said yield enhancing agent may be a nucleoside, preferably, wherein said nucleoside is selected from the group consisting of adenosine, guanosine, uridine, cytidine, inosine, deoxyadenosine, deoxyguanosine, deoxythymidine, deoxycytidine and deoxyinosine.

In a preferred embodiment said nucleoside is selected from the group consisting of adenosine, guanosine, uridine, cytidine, thymidine and inosine. Most preferably, wherein said nucleoside is inosine.

Said yield enhancing agent may be a nucleotide, preferably wherein said nucleotide is selected from the group consisting of adenosine monophosphate (AMP), guanosine monophosphate (GMP), uridine monophosphate (UMP), cytidin monophosphate (CMP), xanthine monophosphate (XMP), inosine monophosphate (IMP), deoxyadenosine monophosphate (dAMP), deoxyguanosine monophosphate (dGMP), thymidine monophosphate (dTMP), deoxycytidin monophosphate (dCMP), deoxyxanththin monophosphate (dXMP) and deoxyinosine monophosphate (dIMP).

In a preferred embodiment said nucleotide is selected from the group consisting of AMP, GMP, UMP, CMP, XMP and IMP. Most preferably, wherein said nucleotide is IMP.

A preferred embodiment is wherein said culture medium comprises at least two yield enhancing agents preferably selected from the group consisting of a purine base, a pyrimidine base, a nucleoside, a nucleotide and derivatives thereof.

Preferably said culture medium comprises at least two yield enhancing agents selected from the group consisting of a nucleoside and a nucleotide. Most preferably wherein said nucleoside is inosine and said nucleotide is IMP.

A preferred embodiment is wherein said culture medium initially comprises from 1 to 70 mM of each yield enhancing agent.

More preferably, wherein said culture medium initially comprises from 1 to 60 mM of each yield enhancing agent, such as from 1.3 to 60 mM, e.g. from 1.5 to 50 mM, preferably from 2 to 40 mM, such as from 2.5 to 30 mM, e.g. from 3 to 20 mM, more preferably from 3 to 15 mM, such as from 4 to 10 mM, e.g. about 7 mM.

Surprisingly, by the method of the present invention it is occasionally possible to obtain LAB cultures that are sufficiently concentrated to be used for production of F-DVS without concentration of the culture. However even when the present method applied most cultures need to be concentrated to obtain starter cultures of commercial interest. Such cultures may preferably be harvested and concentrated by centrifugation or ultra filtration.

In a preferred embodiment the culturing of the microorganism is done at industrial relevant conditions under high Optical Density-conditions.

Accordingly, a preferred embodiment is wherein the Optical Density (OD) of the culture at 600 nm of 1 cm light path medium reached a OD of from $OD_{600}=10$ to $OD_{600}=200$, more preferably a OD of from $OD_{600}=15$ to $OD_{600}=100$, even more preferred a OD of from a OD of from $OD_{600}=20$ to $OD_{600}=90$ and most preferably a OD of from $OD_{600}=25$ to $OD_{600}=80$.

Further, a preferred embodiment is wherein the culturing is done a large-scale fermentor comprising of from 5 L to 100,000 L culture medium, preferably of from 300 L to 20,000 L culture medium.

A preferred embodiment is wherein the culturing comprising control of temperature and/or pH.

Preferably the culture comprises one or more organisms selected from the group comprising *Bifidobacterium* spp., *Brevibacterium* spp., *Propionibacterium* spp., *Lactococcus* spp. including *Lactococcus lactis* subsp. *lactis* and *Lactococcus lactis* subsp. *cremoris*, *Lactobacillus* spp. including *Lactobacillus acidophilus*, *Streptococcus* spp., *Enterococcus* spp., *Pediococcus* spp., *Leuconostoc* spp. and *Oenococcus* spp.

The culture may comprise one or more mesophilic organisms having optimum growth temperatures at about 30° C., preferably one or more mesophilic organisms selected from the group comprising *Lactococcus lactis*, *Lactococcus lactis* subsp. *cremoris*, *Leuconostoc mesenteroides* subsp. *cremoris*, *Pediococcus pentosaceus*, *Lactococcus lactis* subsp. *lactis* biovar. *diacetylactis*, *Lactobacillus casei* subsp. *casei* and *Lactobacillus paracasei* subsp. *paracasei*.

The culture may comprise one or more thermophilic organisms having optimum growth temperatures at about 40° C. to about 45° C., preferably one or more thermophilic organisms selected from the group comprising *Streptococcus thermophilus*, *Enterococcus faecium*, *Lactobacillus delbrueckii* subsp. *lactis*, *Lactobacillus helveticus*, *Lactobacillus delbrueckii* subsp. *bulgaricus* and *Lactobacillus acidophilus*.

Preferably the culture is a LAB-culture that comprises one or more organisms selected from the group comprising

*Lactococcus* spp., *Streptococcus* spp., *Enterococcus* spp., *Lactobacillus* spp., *Leuconostoc* spp., *Pediococcus* spp. and *Bifidobacterium* spp.

The culture may be a LD-culture that comprises one or more organisms selected from the group comprising *Lactococcus lactis* subsp. *lactis*, *Lactococcus lactis* subsp. *cremoris*, *Lactococcus lactis* subsp. *lactis* biovar. *diacetylactis* and *Leuconostoc mesenteroides* subsp. *cremoris*.

The culture may be an O-culture that comprises one or more organisms selected from the group comprising *Lactococcus lactis* subsp. *lactis* and *Lactococcus lactis* subsp. *cremoris*.

In a preferred embodiment the culture is a culture comprising *Lactococcus lactis*.

Commercial starter cultures may commonly be distributed as frozen cultures. At the low temperatures at which such frozen cultures typically are maintained most metabolic activities in the cell ceases and cells can be maintained in this suspended, but viable, state for extended periods.

Concentrated frozen cultures are commercially very interesting since such cultures can be inoculated directly into the production container. By using such concentrated frozen cultures the end-user avoids the otherwise obligatory, time-consuming intermediary fermentation step during which the starter culture are amplified, and the end-user furthermore reduces the risk of contamination drastically. Such concentrated cultures may be referred to as DVS—direct vat Set™ cultures.

As an alternative to the concentrated frozen cultures concentrated freeze dried direct vat Set™ cultures, FD-DVS™, may be prepared. Such cultures have the additional advantage that they can be shipped without refrigeration.

Thus, in a preferred embodiment the method for preparing a microbial culture in increased yields as described herein further comprises:

iii) freezing said harvested microorganism to obtain frozen microbial cells.

Said method may further comprising:

iv) sublimating water from said frozen cells to obtain freeze-dried cells.

Said in another way, wherein the harvested microorganism culture is converted into a freeze-dried cell culture.

The method may further comprise:

v) packing said cells obtained in step iii) or iv).

Often damaging effects of freezing and thawing on the viability of living cells has been observed. In general they are ascribed to cell dehydration and the formation of ice crystals in the cytosol during freezing.

However, a number of cryoprotective agents have been found to ensure that ensure that freezing occur in a controlled and minimally injurious manner, e.g. by ensuring that ice crystallization in the cytosol is precluded or minimized during freezing.

Preferably at least one cryoprotectant is added to the harvested microorganism.

Preferably, the cryoprotective agent(s) is selected from the group consisting one or more compound(s) involved in the biosynthesis of nucleic acids or one or more derivative(s) of any such compounds. Examples of preferred cryoprotective agent(s) suitable to be added to the harvested microorganism corresponds essentially to the preferred yield enhancing agent(s) as described herein. Addition of such cryoprotective agent(s) to harvested microorganism is described in an earlier filed patent application with application number PCT/DK2004/000477. Preferred cryoprotective agent(s) described in PCT/DK2004/000477 are also preferred cryoprotective agent(s) of the present invention. The complete description of PCT/DK2004/000477 is incorporated by reference herein.

An alternative embodiment of the invention is the method of preparing a microbial culture in increased yields as described herein and which further comprise that the harvested microorganism is dried by spray drying, vacuum drying, air drying or any drying process which is suitable for drying of bacterial cultures.

Preferably the starter culture of the second aspect of the invention is provided as a starter culture concentrate, such as a comprising at least $10^8$ CFU of the starter culture organism.

The third aspect the i relates to a culture medium comprising at least one yield enhancing agent selected from the group consisting of a purine base, a pyrimidine base, a nucleoside, a nucleotide and derivatives thereof. Even though a large amount of the yield enhancing agent is consumed during the fermentation it appears that large enough amounts remain in the supernatant of the culture to ensure that a concentrated culture can be identified to be a result of the present method of medium (see example 5 or 6).

Preferably the food product of the fourth aspect of the invention is selected from the group consisting of a milk-based product, a vegetable product, a meat product, a beverage, a fruit juice, a wine and a bakery product.

Preferably the milk-based product is selected from the group consisting of a cheese, yoghurt, a butter, an inoculated sweet milk and a liquid fermented milk product.

In an interesting aspect, the present invention provides a method for obtaining increased yield(s) of microbially produced compound(s), said method comprising the steps of i) culturing a microorganism in a culture medium comprising at least one yield enhancing agent selected from the group consisting one or more compound(s) involved in the biosynthesis of nucleic acids or one or more derivative(s) of any such compounds; and iii) obtaining said microbially produced compound(s), wherein the yield enhancing agent results in an increased yield of microbially produced compound(s) as compared to culturing the microorganism in an identical medium without measurable amounts of the yield enhancing agent.

Compounds produced by microbial organisms as described includes but are not limited to enzymes, proteins, metabolites, glycolipids, antibiotics, bacteriocins, amino acids, flavors, volatiles. Such compounds may be produced by recombinant DNA technology or by conventional means.

The invention is further illustrated in the following non-limiting examples and the figures wherein

EXAMPLES

Figure 1:
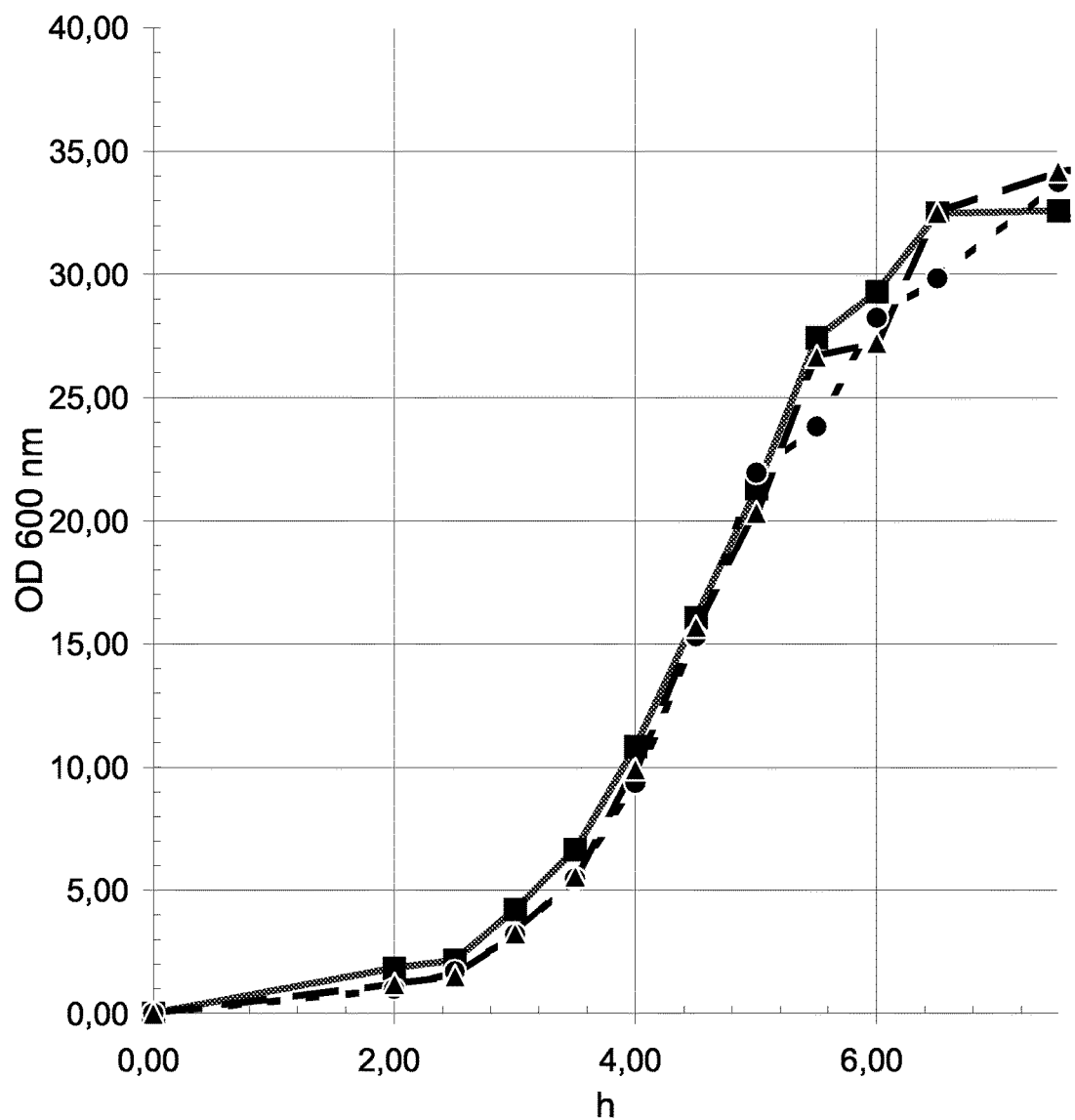
FIG. 1. Shows the yield of three *S. thermophilus* fermentations performed under anaerobic conditions. The graph shows biomass measured as the OD600 of non-concentrated samples of the fermentation medium as a function of time (hours) in the fermentor. Solid triangles indicate addition of 0.2% w/w IMP, solid spheres indicates addition of 0.2% w/w Inosine and solid squares indicates that no yield enhancing agents were added. 0.2% w/w inosine is approximately 7 mM inosine.

Example 1: Yield from Fermentations Performed in Three Different Types of Culture Media To illustrate the effect of adding extra purine containing compounds to an already enriched and optimized media three different types of industrial scale cultures were compared.

All three types of cultures were performed under aeration and in a nutrient medium, in which at least one porphyrin compound is present or is added as described in international patent application WO 00/05342 (the EMIL procedure), and in all instances it was a so-called "O-culture" comprising *Lactococcus lactis* subsp. *lactis* and *Lactococcus lactis* subsp. *cremoris*. O-cultures are typically used to make cheese without holes (Cheddar, Cheshire, Feta). The particular culture is commercially available under the name R 604 from Chr. Hansen A/S, Hoersholm, Denmark (catalogue no. 200113).

The three media are described in table 1

TABLE 1

| culture designation | basic culture medium | added yeast extract | other additives |
|---|---|---|---|
| Old EMIL | BD-5-ex3* | 1.7% w/w standard yeast extract** | |
| New EMIL | BD-5-ex3* | 1.7% w/w new yeast extract** | |
| Super EMIL | BD-5-ex3* | 1.7% w/w new yeast extract** | 0.2% w/w IMP*** 0.2% w/w inosine<sup>αα</sup> |

*BD-5-ex3 is an optimized porphyrin-containing culture medium according to WO 00/05342 and WO 01/52668.
**standard yeast extract and yeast new extract are two commercially available yeast extracts.
***IMP was: inosine-5'-monophosphate (IMP) (Alsiano A/S, Birkeroed, DK).
<sup>αα</sup>inosine was: inosine (Alsiano A/S, Birkeroed, DK).

The culturing was performed in a 550 L or a 10,000 L industrial fermentation tank at 30° C. using 0.5% (w/w) of the culture mentioned above as inoculum. The fermentations were run under aerobic conditions as described in WO 00/05342. The cultures were allowed to acidify to pH 6.2. The pH was subsequently maintained at 6.2 by controlled addition of 13.4 N $NH_4OH$.

When no further base consumption was detected, the respective culture was cooled down to about 10° C.

Following cooling, the bacteria in culture media were concentrated 6-18 times by centrifugation and subsequently frozen as pellets in liquid nitrogen at one atmosphere of pressure to produce a so-called frozen Direct Vat Set culture (F-DVS). The F-DVS pellets were stored at −50° C. until further analysis The yields of the fermentations were specified in two different ways. 1) by the obtained biomass measured as the Optical Density at 600 nm ($OD_{600}$), 2) by kg of F-DVS culture with an "acidification activity" of 4.8-5.1 according to the according to Pearce test described in Example 2: Analytical Procedure QAm-043.

The results are shown in table 2 below.

TABLE 2

Yields of fermentations measured as $OD_{600}$ and

| culture designation | enhancing agent | Biomass ($OD_{600}$) | Yield in kg of F-DVS pr 100 L medium* |
|---|---|---|---|
| Old EMIL | | 32 | 5.56 |
| New EMIL | | 45 | 8.33 |
| Super EMIL | 0.2% w/w IMP 0.2% w/w inosine | 76 | 16.67 |

*the acidification activity of the F-DVS is 4.8-5.1 according to the to Pearce test Conclusion:

From these results it is clear that the addition of an enhancing agent composed of 0.2% w/w IMP and 0.2% w/w inosine, which were added to the culture medium before the start of the aerobic fermentation, results in increased yields.

Example 2: Analytical Procedure QAm-043, Acidification Activity—"Programmed Temperature Profile" Chr. Hansen A/S (Denmark)

Application

This method is used for determination of acidification activity according to Pearce test. The Pearce test is included by the IDF standard (international dairy standard).

Principle

The acidification is performed according to a temperature profile reflecting the temperature course, which the culture will typically encounter when used in the dairy for production of a given dairy product.

For Pearce test this is the cheese making temperature during the production of Cheddar.

pH is measured at a fixed time.

For cultures where rennet is not added during analysis, a continuous pH measurement may be applied.

Analysing Parameters

Analyzing parameters, which are product specific, are given in LIMS.

Definition of temperature profile (for products where Pearce profile is not used).

Control standard to be used.

Type of pH measurement.

Inoculation percents for sample and control standards.

Dilution milk: 206.9 g cold (4° C.) LAB-milk (i.e. UHT-sterilized reconstituted skimmed milk (RSM) containing 9.5% (w/w) solid matter and heated at 99° C. for 30 minutes).

Activity milk: 200 g cold (4° C.) low pasteurized whole milk 3.5% fat.

Rennet: Naturén® standard 190 diluted 1:40 with water.

Apparatus and Reagents pH meter/pH meter for semi continuously pH measurement eks. Radiometer® PHM92.

pH electrode Radiometer® PFC2401.

Buffers: pH 7.00±0.01 and pH 4.01±0.01.

Water bath with a thermostat programmed for heating according to a predetermined temperature profile ±0.2° C.
Temperature sensor.
Balance, precision 0.01 g with minimum two decimals
Watch.
Magnetic stirrer.
Magnets
Beakers, 50 ml.
Small plastic cups.
Rotation apparatus.
Procedure
Preparation of analyze All bottles should be from the same batch i.e. with the same date.

Water bath/s is/are tempered to the initial temperature of the temperature profile to be used.

Bottles for dilution (=first weighing) and for activity (second weighing) are placed at 4° C. until just before use.

Buffers pH 4.01 and pH 7.00 are placed in water bath at the specified measuring temperature ±0.2° C. at least 30 min before calibration of pH meter.

Preparation of samples before analysis.

Frozen cultures:

Frozen samples/control standards are before first weighing placed in a foam box with dry ice and are kept here till all weighings are done.

Frozen cultures, which are thawn before use:

For frozen products, where a whole carton is used, the product is thawn according to current instructions.

After thawing the sample may be kept at 4° C. for max. 30 min, before use.

Freeze dried cultures:

Freeze dried samples and control standards are acclimatized at room temperature for at least 15 min before start of analysis.

Provided that the sample are going to be used for retest the day after, it may be stored at +8° C.

Inoculation procedure

Weighing of product/control standard is carried out directly into the milk.

The actual amount of inoculum (1st weighing) is entered with at least two decimals.

Frozen and thawn products are turned carefully about 4 times, after which the bottle stands for approx. 50 sec.

For freeze dried products the rotation apparatus must be used. It has to be driven with frequent speed for 5 minutes or till the product is completely soluted. This is controlled by leaving the bottle on the table for a moment and then checking the solution by looking in the bottom of the bottle.

Note:

If convenient for the working routine a cold, first weighing can stand at room temperature for max. 15 minutes before second weighing.

2nd weighing:

The dilution bottle is turned before 2. weighing is carried out.

The actual amount of inoculum (2nd weighing) is entered with at least 2 decimals.

The activity bottle is turned and the inoculation procedure is repeated for samples/control standards.

Activity bottles, which are inoculated from the same 1st weighing, are inoculated in succession.

2 ml rennet is added each bottle either before or after 2. weighing. After this the bottles are turned so the rennet been distributed.

The bottles are subsequently incubated at one time, as described in 6.

In the end 2 uninoculated milk bottles are placed in a water bath; one for measuring of the water bath temperature and one for measuring pH in the blind milk.

Incubation

Note: When more water baths are required, the control standard with corresponding samples MUST be incubated in the same water bath.

All activity bottles are incubated at the same time in a pre-heated water bath at the defined starting temperature for the temperature profile.

The temperature profile is started at the same time as the bottles are placed in the water bath.

Hereafter the incubation temperature is controlled by a thermostat programmed for following a certain temperature profile. For Pearce test see table 3.

The water level in the water bath should be min. 2 cm higher than the surface of the milk.

TABLE 3

Temperature program in Pearce profile (following the IDF)

| Time, minutes | Temperature, ° C. | Variation |
|---|---|---|
| 0 | 31.0 | ±0.2° C. |
| 50 | 31.0 | ±0.2° C. |
| 54 | 31.7 | ±0.5° C. |
| 58 | 32.2 | ±0.5° C. |
| 62 | 32.8 | ±0.5° C. |
| 66 | 33.3 | ±0.5° C. |
| 70 | 33.9 | ±0.5° C. |
| 73 | 34.4 | ±0.5° C. |
| 76 | 35.0 | ±0.5° C. |
| 79 | 35.6 | ±0.5° C. |
| 82 | 36.1 | ±0.5° C. |
| 85 | 36.7 | ±0.5° C. |
| 87.5 | 37.2 | ±0.5° C. |
| 90 | 37.8 | ±0.2° C. |
| 360 | 37.8 | ±0.2° C. |

Calibration of pH Electrode

Calibration is carried out at initial temperature according to current instructions regarding electrode calibration and maintenance.

Measurement of pH

After incubation the bottles are shaken well and pH is measured.

The pH measurement is carried out in the bottle or in a sample, which is poured into a 50 ml beaker with magnet stirring.

pH is entered with at least 2 decimals.

Possible remarks on the measurement are entered.

The measuring procedure is continued till all samples/control standards and the uninoculated milk are measured.

Finally pH in buffers are measured and entered.

Continuous pH measurement

The pH values are sampled from the moment, the temperature profile is started. After the incubation is completed, the measured pH values in both buffers at initial temperature are registered.

Example 3: Yield of *Lactococcus lactis* Fermentations Performed at Standard Anaerobic High-OD Conditions To illustrate the effect of adding extra purine containing compounds to an already enriched and optimized media two different types of industrial scale fermentation were compared, one with and one without 0.3% w/w inosine added.

Culture:

The present experiment was performed using the commercially available R 604 culture, which is available from Chr. Hansen A/S, Hoersholm, Denmark (catalogue no. 200113).

Fermentation Medium:

The cultures were cultured in a medium having the following composition: Casein hydrolysate (Oxoid, Basingstoke, UK, Product Code L41), 30 g/l; Primatone RL (Quest, Naarden, The Netherlands, Product Code 5X59051), 30 g/l; soya peptone (Oxoid, Basingstoke, UK, Product Code L44), 30 g/l; yeast extract (Oxoid, Basingstoke, UK, Product Code L21), 15 g/l; MgSO4, 1.5 g/l; Na-ascorbate, 3 g/l; and lactose 50 g/l.

The medium was sterilized by UHT-treatment (143° C. for 8 sec.). The finished medium had a pH of 6.5.

Fermentation Condition the Cultures:

The fermentation was performed in a 550 L industrial fermentation tank without aeration at 30° C. using 1% (w/w) of the culture mentioned above as inoculum. At high OD conditions the fermentation is essentially anaerobic. The cultures were allowed to acidify to pH 6.0. The pH was subsequently maintained at 6.0 by controlled addition of 13.4 N $NH_4OH$.

When no further base consumption was detected, the respective culture was cooled down to about 10° C.

Following cooling, the bacteria in culture media were concentrated 6-18 times by centrifugation and subsequently frozen as pellets in liquid nitrogen at one atmosphere of pressure to produce a so-called frozen Direct Vat Set culture (F-DVS). The F-DVS pellets were stored at −50° C. until further analysis The yields of the fermentations were specified in two different ways:

1) by the obtained biomass measured as the Optical Density at 600 nm (OD600), or
2) by kg of F-DVS culture pr. 100 L fermentation medium wherein the F-DVS culture have an "acidification activity" of 4.8-5.1 according to the Pearce test described in Example 2: Analytical Procedure QAm-043.

The results are shown in the table 4 below.

TABLE 4

| culture designation | extra additive to fermentation medium | Yield as OD600 | Yield according to Pearce[§] |
|---|---|---|---|
| PP11145 | nothing | 25.1 | 4.95 |
| PP11146 | 0.3% w/w inosine[@] | 25.2 | 4.98 |

[@]inosine was: inosine (Alsiano A/S, Birkeroed, DK).
[§]see example 2

Conclusion:

From these results it was clear that the addition of an enhancing agent composed of 0.3% w/w inosine, which were added to the anaerobic culture medium before the start of the fermentation, did not result in increased yields.

Example 4: Yield of Streptococcus thermophilus Fermentations Performed at Standard Anaerobic High-OD Conditions This experiment was performed to investigate the effect of adding extra purine containing compounds to an already enriched and optimized media to be used for anaerobic fermentation at high OD-conditions. In the present experiment three cultures of Streptococcus thermophilus were prepared, one with 0.2% w/w inosine added, one with 0.2% w/w IMP added and one culture where no extra purine containing compounds were added to the medium.

Culture:

The present experiment was performed using the commercially available Streptococcus thermophilus culture CHQ-18, which is available from Chr. Hansen A/S, Hoersholm, Denmark.

Fermentation Medium:

The cultures were cultured in a rich medium based on complex medium components, BioSpringer yeast extract 207, Arla skim milk powder (Milex 240), and lactose.

The medium was sterilized by UHT-treatment (143° C. for 8 sec.). The finished medium had a pH of 6.0.

Fermentation Condition of the Cultures:

The fermentation was performed in a 3 L agitated fermentation tank at 40° C. using 0.1% (w/w) of the culture mentioned above as inoculum. The pH was maintained at 6.0 by addition of 13.4 N $NH_4OH$. Anaerobic conditions were ensured by flushing with nitrogen in head space (1.5 l/min). Agitation was 300 rpm.

The yields of the fermentations were specified by the obtained biomass measured as the Optical Density at 600 nm (OD600) of unconcentrated samples sampled during the fermentation.

The result of the three fermentations is shown in FIG. 1 below.

Conclusion:

From these results it appears that the addition of an enhancing agent composed of either 0.2% w/w inosine or 0.2% w/w IMP did not result in increased yields.

Figure 2:
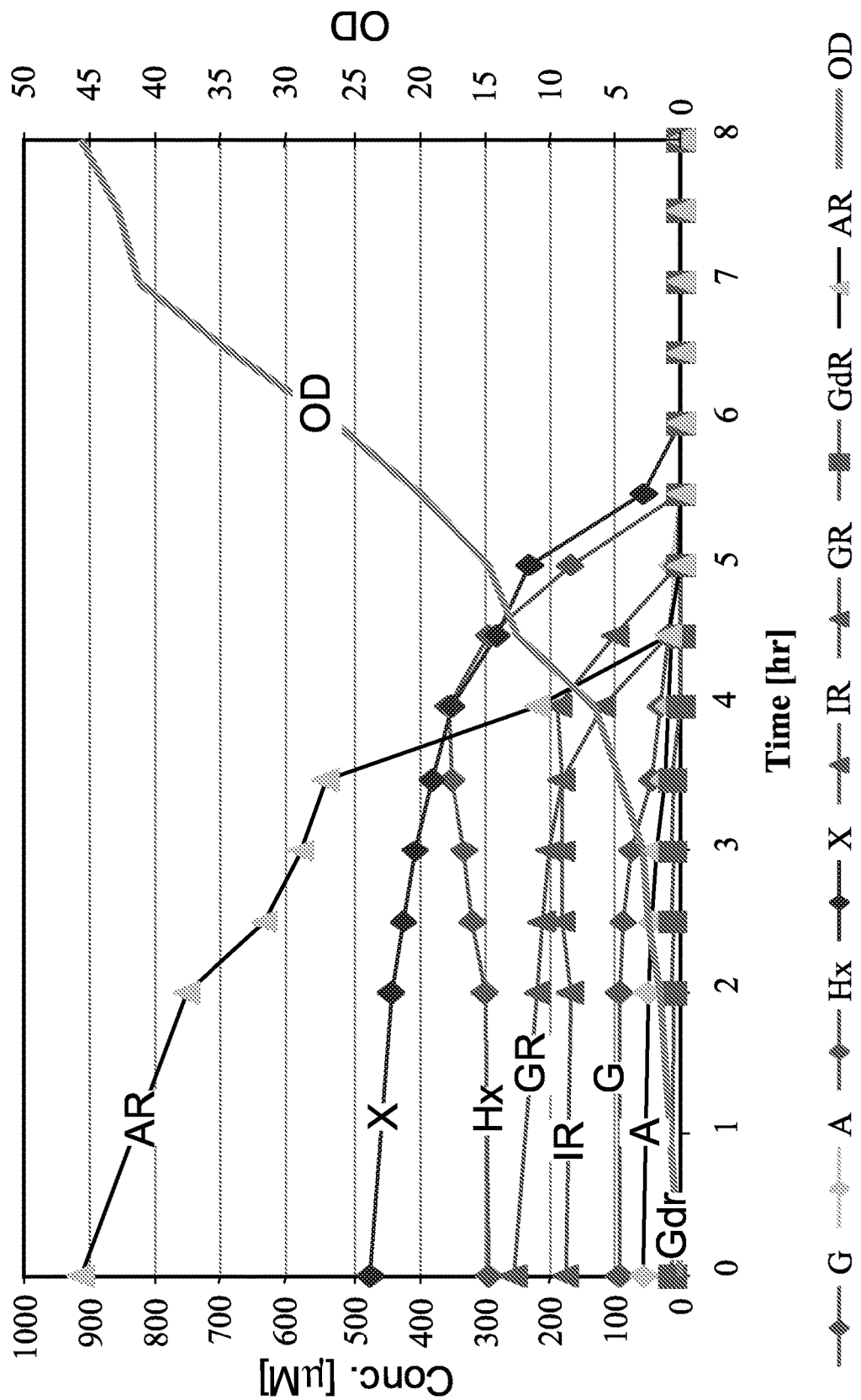
FIG. 2. The level of various nucleo compounds and the Optical density during fermentation in a rich complex medium comprising relatively high amounts of purines. Briefly, a *Lactococcus lactis* (strain CHCC2862) was grown aerobically in the complex medium containing yeast extract and other complex components. The concentration in μM (primary axis) and OD600 (secondary axis) is plotted against time. Abbreviations: G, guanine; A, adenine; Hx, hypoxanthine; X, xanthine; IR, inosine; GR, guanosine; GdR, deoxyguanosine; AR, adenosine.

Example 5: Use of Chemical Analysis for Detection of the Presence of Excess Nucleo Compounds in a Fermentation Even though lactic acid bacteria in general are prototrophic for purine and pyrimidines, and can thus synthesize these compounds, the cells utilize available exogenous purine and pyrimidine sources during fermentation. Specifically, all common purine nucleo compounds may be completely depleted already around OD 15 (see FIG. 2). Interestingly, the biomass accumulation continues to around OD 45 even though the purine compound is depleted. A similar result is found for the pyrimidine compounds (data not shown). This means that the fermentation broth (i.e. fermentate without cells) at the end of growth is devoid of purine and pyrimidine compounds.

Figure 3:
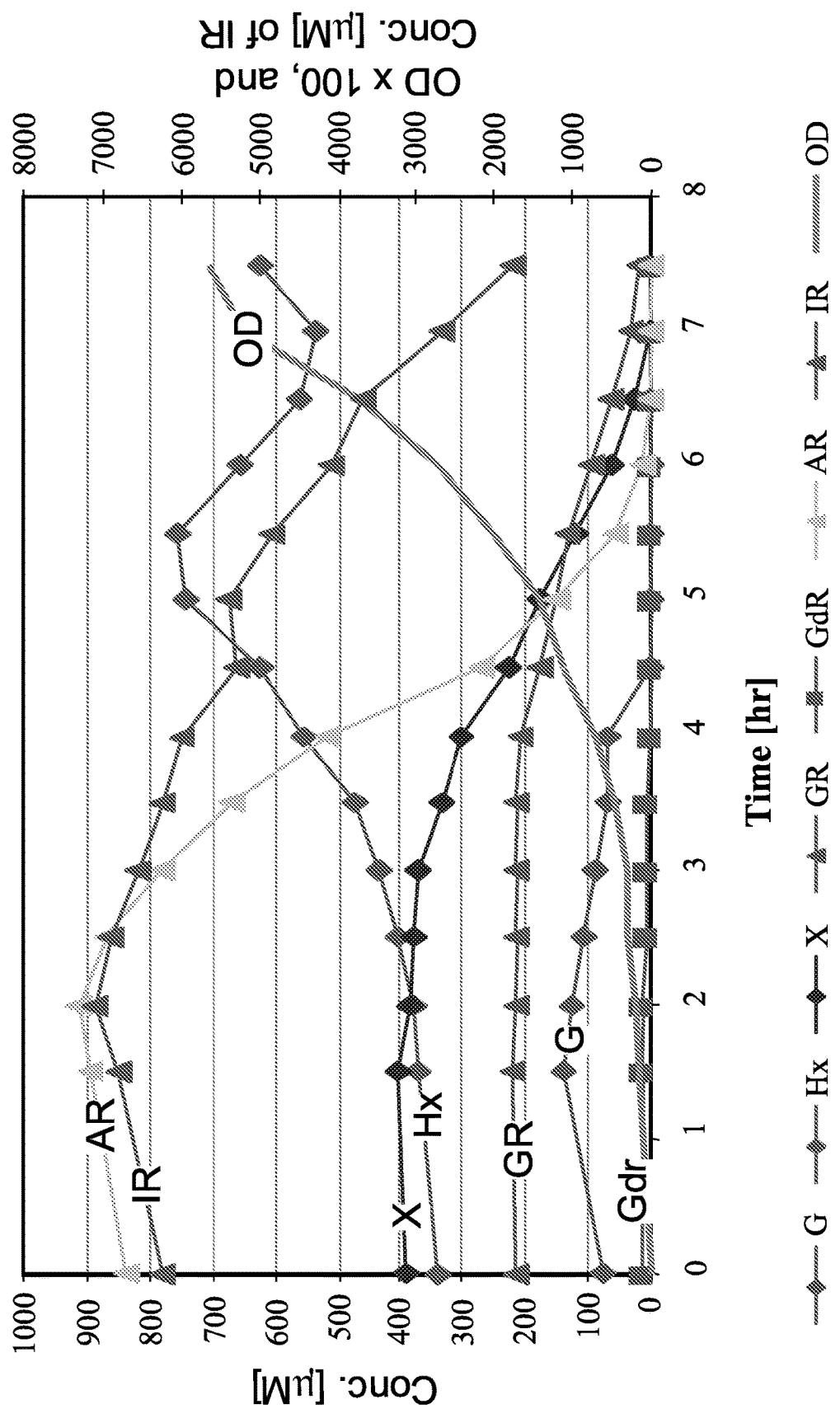
FIG. 3. The level of purine compounds during fermentation with 2 g/L of inosine added to the medium. Briefly, a *Lactococcus lactis* (strain CHCC2862) was grown aerobically in the same complex medium as used in FIG. 2 except that 2 g inosine pr. L medium was added. The concentration in μM (primary axis) and OD600×100 (secondary axis) is plotted against time. Note that the level of inosine is indicated by the secondary axis. Abbreviations: G, guanine; A, adenine; Hx, hypoxanthine; X, xanthine; IR, inosine; GR, guanosine; GdR, deoxyguanosine; AR, adenosine and IR, inosine (note different axis for inosine).

If on the other hand for example inosine is added in excess to the growth medium this compound, and/or the corresponding nucleo base hypoxanthine (present due to hydrolysis of the inosine), will be present in the fermentation broth at the end of growth (see FIG. 3). Such excess nucleo compounds may easily be detected in the fermentation broth.

For the production of for example F-DVS the cells in the fermentate are concentrated several-fold. Although, the cells are present in a several-fold higher level in the F-DVS than in the fermentate substantial amounts of fermentation broth is still present in the F-DVS. This pure fermentation broth can be obtained through further concentrating the cells. Useful methods for isolating the broth may be through defrosting the F-DVS and then use a filter or by using a higher g-force during centrifugation than was used through production of the F-DVS.

With just small amounts of pure broth available it can be tested if any nucleo compounds were present in the fermentate, and thus is such compounds had been added in excess to the fermentation medium. Such detection method may be conventional HPLC (see for example http://www.laubscher-labs.com/Presentation/YMC%20ODS-AQ.pdf) where the common nucleo bases and nucleosides (cytosine, cytidine, uracil, deoxycytidine, guanine, adenine, hypoxanthine, uridine, xanthine, thymine, inosine, guanosine, deoxyinosine, deoxyguanosine, xanthosine, thymidine, adenosine, and deoxyadenosine) can be conveniently detected. Other available methods may be used for the detection of the corresponding nucleotides. The presence of either of these compounds in the broth will strongly indicate that the fermentation has been performed according to the present invention.

Example 6: Use of Proteomics for Detection of the Presence of Excess Nucleo Compounds in a Fermentation During growth the cells require a continuous flow of purine and pyrimidine nucleotides for synthesis of RNA and DNA. These nucleotides can either be supplied exogenously from the medium (salvage) or be synthesized de novo from simpler compounds. For the de novo synthesis the specific de novo synthesis genes must be expressed. Conversely, the genes do not have to be expressed when an exogenous source is present.

In the case of purine de novo synthesis around 10 gene-products are involved. It has previously been found that the purDEK operon involved in the purine de novo synthesis in *L. lactis* is about 35-fold regulated depending on the presence/absence of an exogenous purine source (Nilsson & Kilstrup 1998). Also, the presence/absence of several purine de novo synthesis proteins on 2D protein gels has been found to depend on the availability of exogenous purines (Gitton et al. 2005).

To set up a specific method for detection of the presence/absence of exogenous purines in the medium we inoculated *L. lactis* subsp. *lactis* CHCC2862 into defined SA medium with 1% glucose. This medium is devoid of nucleo compounds (Jensen & Hammer 1993). Cultures were set up at 30° C. with and without 0.2% inosine and incubated overnight. Exponentially growing cells were then inoculated into fresh medium at an OD600 of around 0.1. At OD 0.8 (exponential growth) and in stationary phase cells were harvested and 2D protein gels were produced.

In general around 3-400 protein spots were detectable on the gels with the pH range 4-7. For OD 0.8 there were less than 10 spots that were present from the culture without inosine, but absent (or very weak) from the culture with inosine. The presence/absence pattern of these spots indicates that the respective proteins are only present when there is no exogenous purine source. Four of the strongest spots present only on the gel produced from the culture without purines were subjected to in-gel digestion and mass spectrometry identification. The proteins were identified as: purH (bifunctional purine biosynthesis protein), purM (phosphoribosylaminoimidazole synthase), yphF (phosphoribosylformylglycinamidine synthase PurS), and fhs (formyltetrahydrofolate synthetase). The gene-products of the three genes purH, purM and yphF (purS) are all directly involved in the purine de novo biosynthesis, whereas fhs is involved in the formation of one-carbon units, which are used for purine de novo synthesis. For the cells in stationary phase, which is similar to the situation found in F-DVS, a similar absence/presence pattern was obtained. Overall, this shows that the presence of excess nucleo compounds in a medium can be detected using proteomics.

Whereas the present examples illustrate the detection of yield enhancing purines a similar detection of the presence of an excess of pyrimidines can easily be set up. Thus proteomics can be used to provide very strong indications of a fermentation that has been performed according to the present invention.

Materials & Methods

The methods described below are based on standard methods published previously (Fey at al. 1998; Vido et al. 2004; Gitton et al. 2005).

Preparation of cell free extract. Cells were harvested by centrifugation and washed twice in ice-cold 10 mM Tris-HCl, pH 7, 0.25 M sucrose. Cells were transferred to a 2 mL Eppendorf tube containing approx. 1.0 g glass beads (0.25-0.50 mm) and shaken in a mixer mill for two times 6 min. Subsequently, the extracts were centrifuged at 10,000 rpm for 5 min and 250-300 µL supernatant was transferred to a new Eppendorf tube. The supernatant was centrifuged once more at 15,000 rpm for 5 min and all except 10-20 µl from the bottom of the tube was transferred to yet a new Eppendorf tube. DTT was added from a 1 M stock solution to a final concentration of 10 mM and the lysate stored frozen at −20° C.

2D gel electrophoresis (isoelectric focusing and gel electrophoresis). For each gel between 75 and up to 300 µg of protein was precipitated by a chloroform/methanol procedure and resuspended in 190 µl rehydration buffer (8 M urea, 50 mM DTT, 4% CHAPS, 0.2% carrier ampholytes). First dimension was run on 11 cm IPG strips pH 4-7 and pH 4.7-5.9 from Bio-Rad with active rehydration for 12 hours followed by the standard program for 11 cm strips on a Protean IEF cell from Bio-Rad. For strips of pH 3.9-5.1, the proteins were cup loaded after the strips were rehydrated. After IEF electrophoresis the strips were either stored frozen at −20° C. or directly prepared for electrophoresis in the second dimension.

The strips were equilibrated in SDS buffer prior to second dimension PAGE for 2×15 min, first in the presence of DTT, second in excess of IAA. Thereafter the strips were attached to 10-20% and 12.5% polyacrylamide gels (Criterion Tris-HCl from Bio-Rad) by agarose sealing, and the second dimension was run at 200V for one hour on a Criterion Dodeca Cell. The gels were stained in BioSafe Coomassie and scanned on a densitometer GS-800 from Bio-Rad.

Identification of proteins. The identity of proteins in chosen spots was determined by in-gel digestion and analysis of peptide profile and amino acid content using mass spectrometry. The generated data were subsequently used for searching in public databases for proteins with similar properties (Alphalyse A/S, Odense, Denmark)

REFERENCES

Fey, S. J., A. Nawrocki, M. R. Larsen, A. Gorg, P. Roepstorff, G. N. Skews, R. Williams, and P. M. Larsen. 1997. Proteome analysis of *Saccharomyces cerevisiae*: a methodological outline. Electrophoresis 18:1361-1372.

Gitton, C., M. Meyrand, J. Wang, C. Caron, A. Trubuil, A. Guillot, and M. Y. Mistou. 2005. Proteomic signature of *Lactococcus lactis* NCDO763 cultivated in milk. Appl Environ Microbiol 71:7152-7163.

Jensen, P. R. and Hammer, K. 1993. Minimal requirements for exponential growth of *Lactococcus lactis*. Appl. and Env. Microbiol. 59:4363-4366.

Nilsson D. and Kilstrup M. 1998. Cloning and expression of the *Lactococcus lactis* purDEK genes, required for growth in milk. Appl Environ Microbiol. 64:4321-4327.

Vido, K., D. Le Bars, M. Y. Mistou, P. Anglade, A. Gruss, and P. Gaudu. 2004. Proteome analyses of heme-dependent respiration in *Lactococcus lactis*: involvement of the proteolytic system. J Bacteriol 186:1648-1657.

The invention claimed is:

1. A method for obtaining harvested *Lactococcus lactis* subsp. *lactis* bacteria and/or *Lactococcus lactis* subsp. *cremoris* bacteria, comprising:
   (i) culturing one or more of *Lactococcus lactis* subsp. *lactis* bacteria and *Lactococcus lactis* subsp. *cremoris* bacteria by aerating the culture in the presence of oxygen at conditions that allow the fermentation to proceed beyond an Optical Density measured at 600 nm ($OD_{600}$) of 10,
   wherein said culture medium comprises:
   yeast extract;
   at least one porphyrin compound; and
   at least one yield-enhancing agent at a concentration that is from 1 mM to 70 mM at the initiation of the fermentation and that is sufficient to yield at least 1 μM of said at least one yield-enhancing agent in the bacteria culture at the termination of the fermentation, wherein said at least one yield-enhancing agent is selected from the group consisting of inosine, inosinate (IMP), deoxyinosine, and deoxyinosinate (dIMP), wherein the $OD_{600}$ is at least 10 at the termination of the fermentation; and
   (ii) harvesting said bacteria to obtain harvested *Lactococcus lactis* subsp. *lactis* bacteria and/or *Lactococcus lactis* subsp. *cremoris* bacteria.

2. The method according to claim 1, wherein said culture medium comprises at least two yield-enhancing agents.

3. The method according to claim 2, wherein two of said at least two yield-enhancing agents are inosine and IMP.

4. The method according to claim 1, wherein said culture medium initially comprises an amount of said at least one yield-enhancing agent selected from the group consisting of 1 to 60 mM, 1.3 to 60 mM, 1.5 to 50 mM, 2 to 40 mM, 2.5 to 30 mM, 3 to 20 mM, 3 to 15 mM, 4 to 10 mM, and about 7 mM.

5. The method according to claim 1, wherein the $OD_{600}$ of the culture medium at the termination of fermentation is selected from the group consisting of $OD_{600}$=10 to $OD_{600}$=200, $OD_{600}$=15 to $OD_{600}$=100, and $OD_{600}$=20 to $OD_{600}$=80.

6. The method according to claim 1, wherein the *Lactococcus lactis* subsp. *lactis* bacteria and/or *Lactococcus lactis* subsp. *cremoris* bacteria are *Lactococcus lactis* subsp. *cremoris* bacteria.

7. The method according to claim 1, wherein the *Lactococcus lactis* subsp. *lactis* bacteria and/or *Lactococcus lactis* subsp. *cremoris* bacteria are *Lactococcus lactis* subsp. *lactis* bacteria.

8. The method according to claim 1, further comprising freezing said harvested *Lactococcus lactis* subsp. *lactis* bacteria and/or *Lactococcus lactis* subsp. *cremoris* bacteria to obtain frozen *Lactococcus lactis* subsp. *lactis* bacteria and/or *Lactococcus lactis* subsp. *cremoris* bacteria.

9. The method according to claim 8, further comprising sublimating water from the frozen *Lactococcus lactis* subsp. *lactis* bacteria and/or *Lactococcus lactis* subsp. *cremoris* bacteria to obtain freeze-dried *Lactococcus lactis* subsp. *lactis* bacteria and/or *Lactococcus lactis* subsp. *cremoris* bacteria.

10. The method according to claim 8, further comprising packing the frozen *Lactococcus lactis* subsp. *lactis* bacteria and/or *Lactococcus lactis* subsp. *cremoris* bacteria.

11. The method according to claim 8, wherein at least one cryoprotectant is added to the harvested *Lactococcus lactis* subsp. *lactis* bacteria and/or *Lactococcus lactis* subsp, *cremoris* bacteria prior to freezing.

12. The method according to claim 1, wherein the at least one yield-enhancing agent is selected from the group consisting of inosine and inosinate (IMP).

* * * * *